United States Patent [19]
Ashihara et al.

[11] Patent Number: 6,017,494
[45] Date of Patent: Jan. 25, 2000

[54] LIQUID SUPPLY DEVICE AND ANALYTICAL TEST DEVICE

[75] Inventors: Yoshihiro Ashihara; Mitsushi Gotanda, both of Saitama; Akira Hasegawa; Yuko Fujiwara, both of Tokyo, all of Japan

[73] Assignee: Fujirebio Inc., Tokyo, Japan

[21] Appl. No.: 09/065,725

[22] Filed: Apr. 24, 1998

[51] Int. Cl.$^7$ .......................... G01N 31/22; G01N 21/29
[52] U.S. Cl. ................... 422/58; 436/169; 422/56
[58] Field of Search .................... 422/56, 58, 61; 436/164, 169

[56] References Cited

U.S. PATENT DOCUMENTS

| | | |
|---|---|---|
| 5,204,063 | 4/1993 | Allen . |
| 5,726,010 | 3/1998 | Clark . |
| 5,750,333 | 5/1998 | Clark . |

OTHER PUBLICATIONS

Exhibit 1, "Trademark Espline HBsAg", 1 page, Sep. 29, 1997.
Exhibit 2, "Espline HBsAg, HBsAb", 8 pages . No Date
Exhibit 3, "Espline HBsAg", 2 pages . No Date

*Primary Examiner*—Robert J. Warden, Sr.
*Assistant Examiner*—Jennifer McNeil
*Attorney, Agent, or Firm*—Oblon, Spivak, McClelland, Maier & Neustadt, P.C.

[57] ABSTRACT

A liquid supply device for transporting a liquid to a predetermined portion includes a liquid container for holding a liquid therein, which has an opening, a sealing sheet member which is impermeable but rupturable and seals the opening of the container, and an absorbent material which is capable of transporting the liquid by capillary action, the absorbent material being disposed on the sealing sheet member, out of contact with the liquid when the sealing sheet member is not ruptured, while when the sealing sheet member is ruptured and the absorbent material is brought into contact with the liquid, part of the absorbent material being continuously held within the liquid and transporting the liquid to the predetermined position. An analytical test device using the above liquid supply device is provided, which may be used, for instance, immunoassay.

13 Claims, 4 Drawing Sheets

PRIOR ART FIG. 1(a)
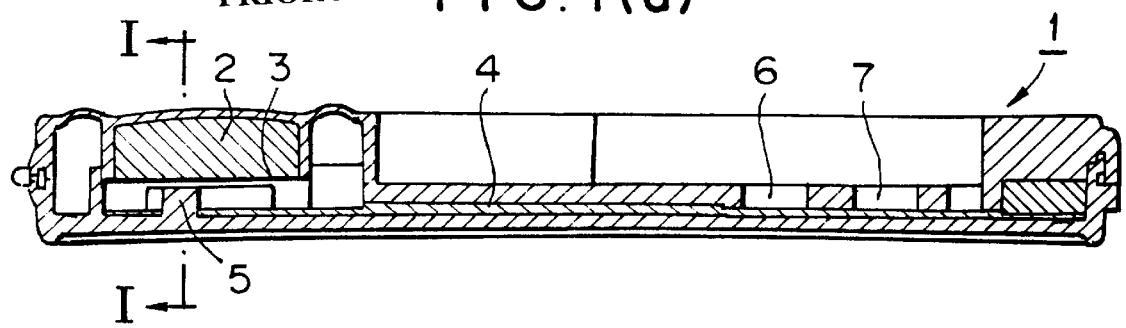
PRIOR ART FIG. 1(b)
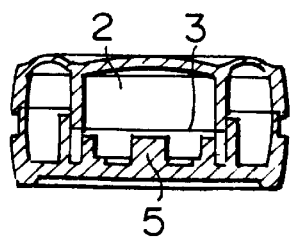
PRIOR ART FIG. 1(c)
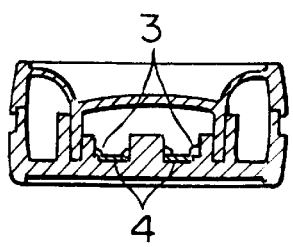
PRIOR ART FIG. 2
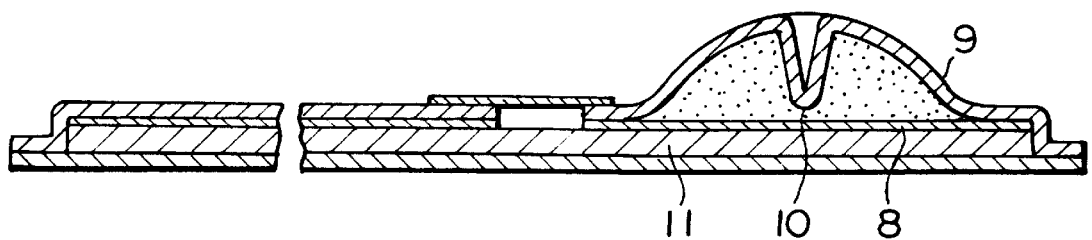

FIG. 3(a)     FIG. 3(b)     FIG. 3(c)
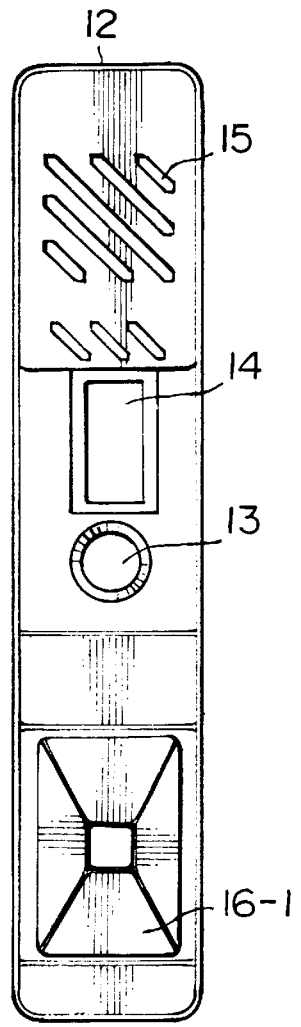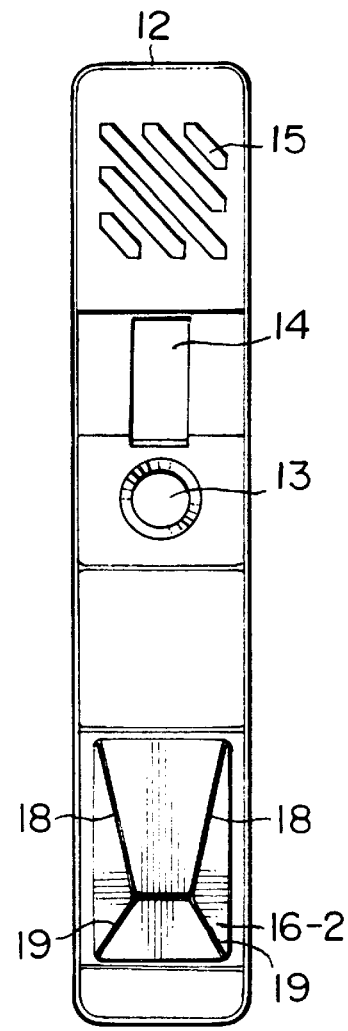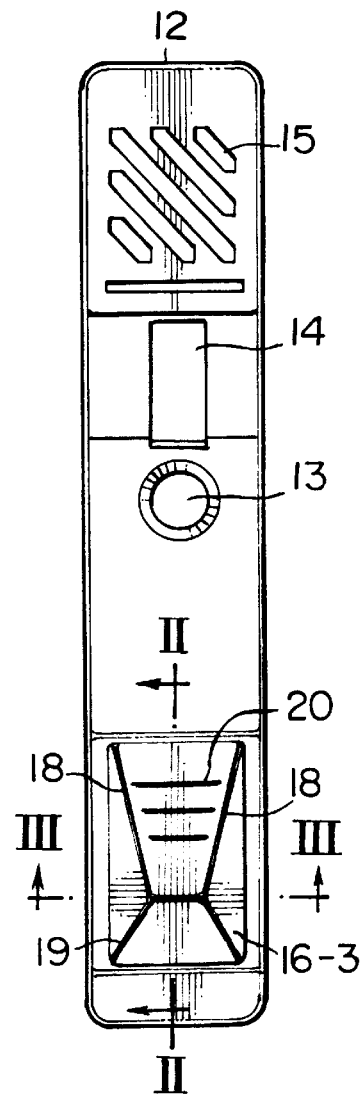
FIG. 3(d)
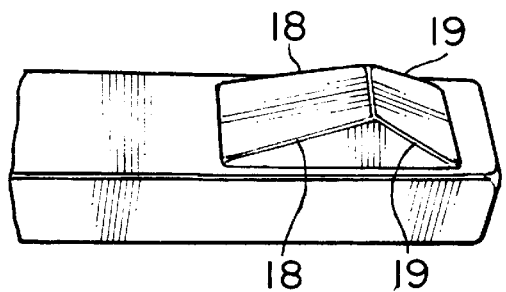

LIQUID SUPPLY DEVICE AND ANALYTICAL TEST DEVICE

BACKGROUND OF THE INVENTION

1. Field of the Invention

The present invention relates to a liquid supply device and an analytical test device for analyzing a test substance in a test sample, which uses the liquid supply device.

2. Discussion of Background

Disposable analytical test devices, which are compact and capable of easily analyzing test substances in test samples, have conventionally been employed. In such conventional analytical test devices, there are analytical test devices of such a type that can elute a test substance to be detected in a test sample, using a developing liquid, and transport the test substance to a detecting portion where the test substance is detected, which are particularly used for immunoassay.

For instance, in Japanese registered design 887,647, there is disclosed an analytical test device which is used for analyzing a fluid portion of the blood such as serum in the field of clinical examination. More specifically, as shown in FIG. 1(a), a pot 2 sealed with a film 3, closing a liquid reagent therein, is incorporated in a plastics case 1. The pot 2 sealed with the film 3 is situated above an absorbent material strip 4, with the film 3 being directed downward. The analytical test device of this type is referred to as a "liquid pot upper type" test device. When this analytical test device is actually used, the pot 2 is depressed downward in such a manner that the pot 2 is moved from a position shown in FIG. 1(b) to a position shown in FIG. 1(c), so that the film 3 is ruptured by a projected portion 5 as shown in FIG. 1(c). As a result, the liquid reagent flows out of the pot 2 onto the absorbent material strip 4. The liquid reagent moves along the absorbent material strip 4 by capillary action, and a test substance contained in a test sample 6 is moved up to a detection portion 7 together with the liquid reagent, so that the result of a reaction of the test substance and the liquid reagent can be observed from above the detection portion 7.

Japanese Laid-Open Application 63-223559 (corresponding to U.S. Pat. No. 4,965,047) discloses an analytical test device as shown in FIG. 2, which comprises a plastics blister 9 holding a liquid reagent therein, provided with a sealing member 8 at a lower side of the plastics blister 9 as shown in FIG. 2. The analytical test device of this type is referred to as a "spike-rupturable vacuum type" analytical test device. When this analytical test device is actually used, the blister 9 is depressed so as to rupture the sealing member 8 with a spike 10 located within the blister 9, and the liquid reagent is caused to flow onto an absorbent material strip 11 which is disposed below the sealing member 8.

In the above-mentioned two types of the analytical test devices, the liquid reagent is applied to the fixed absorbent material strip by depressing the pot or deforming the blister, so that when the pot is depressed with too much force or the blister is abruptly deformed, a large quantity of the liquid reagent is rushed through the ruptured sealing film or member onto the absorbent material strip and is caused to flow along the absorbent material strip not only from a front side and a back side, but also from both sides of the absorbent material strip. The result is that it may occur that the liquid reagent is not sufficiently developed up to the detecting portion and does not sufficiently react with the test substance in the test sample.

In particular, in the case of the "spike-rupturable vacuum type" analytical test device, sufficient development cannot be achieved one time per four times of the tests and even when the sealing member is ruptured, it may occur that a relatively large quantity of the liquid reagent stays in the blister.

In the case of the "liquid pot upper type" test device, the reproducibility of the developing rate is poor.

SUMMARY OF THE INVENTION

It is therefore a first object of the present invention to provide a liquid supply device capable of transporting a liquid to a predetermined portion along an absorbent material in a stable manner and quickly.

A second object of the present invention is to provide an analytical test device for analyzing a test substance in a test sample, free of the above-mentioned conventional problems, capable of performing accurate analysis with sufficient development of the liquid reagent and excellent reproducibility of the developing rate.

The first object of the present invention can be achieved by a liquid supply device for transporting a liquid to a predetermined portion, comprising:

a liquid container for holding a liquid therein, which comprises an opening, a sealing sheet member which is impermeable but rupturable and seals the opening of the container, and an absorbent material which is capable of transporting the liquid by capillary action, the absorbent material being disposed on the sealing sheet member, out of contact with the liquid when the sealing sheet member is not ruptured, while when the sealing sheet member is ruptured and the absorbent material is brought into contact with the liquid, part of the absorbent material being continuously held within the liquid and transporting the liquid to the predetermined position.

The above liquid supply device may further comprise a rupturing member which is capable of engaging with the absorbent material, rupturing the sealing sheet member and holding part of the absorbent material within the liquid.

The liquid supply device may further comprise a deformable supporting member for supporting the rupturing member. The deformable supporting member comprises a convex portion which can be irreversibly inverted into a concave form when depressed, thereby holding the rupturing member in such a position that the sealing sheet member is ruptured and part of the absorbent material is continuously held within the liquid.

The deformable supporting member may comprise at least one groove-shaped portion for facilitating the irreversible inverting of the convex portion into the concave form and maintaining the concave form when depressed.

The second object of the present invention can be achieved by an analytical test device which comprises:

a liquid supply device comprising:

a) a liquid container for holding a liquid therein, which comprises an opening, b) a sealing sheet member which is impermeable but rupturable and seals the opening of the liquid container, and c) an analytical test strip comprising an absorbent material, which is capable of transporting the liquid by capillary action, the analytical test strip being disposed on the sealing sheet member, out of contact with the liquid when the sealing sheet member is not ruptured, while when the sealing sheet member is ruptured and the analytical test strip is brought into contact with the liquid, part of the test strip being continuously held within the liquid and transporting the liquid to the predetermined position, a test sample application portion to which a test sample which may contain a test substance to be detected is applied so that the test sample is brought into contact with the liquid which is transported by the analytical test strip, and a detecting portion for detecting a predetermined condition of the test sample in contact with one or more reagents applied to the analytical test strip at a predetermined portion upstream of the detecting portion and carried thereto by the liquid.

The liquid supply device for the analytical test device may further comprise a rupturing member which is capable of engaging with the analytical test strip, rupturing the sealing sheet member and holding part of the analytical test strip within the liquid.

The liquid supply device for the analytical test device may further comprise a deformable supporting member for supporting the rupturing member. The deformable supporting member comprises a convex portion which can be irreversibly inverted into a concave form when depressed, thereby holding the rupturing member in such a position that the sealing sheet member is ruptured and part of the analytical test strip is continuously held within the liquid.

It is preferable that the deformable supporting member in the liquid supply device comprise at least one groove-shaped portion for facilitating the irreversible inverting of the convex portion into the concave form and maintaining the concave form when depressed.

The above-mentioned one or more reagents may be applied to the absorbent material at the test sample application portion.

The above-mentioned one or more reagents may also be contained in the liquid in the liquid container.

The analytical test device may further comprise a vaporization portion, which is disposed downstream of the detecting portion with respect to the flow of the liquid through the analytical test strip, wherein the area of the vaporization portion is larger than the total of the areas of the test sample dropping portion and the detecting portion.

The analytical test strip for the analytical test device may comprise a plurality of absorbent portions, each of which is capable of transporting the liquid by capillary action.

It is preferable that the analytical test strip comprise:

a first absorbent portion comprising a substrate for a specific enzyme, part of the first absorbent portion being disposed on the sealing sheet member, a second absorbent portion on which a first material which specifically binds with the test substance contained in the test sample is immobilized, the second absorbent portion being disposed upstream of the test sample application portion, and connected to the first absorbent portion, without being brought into contact with the liquid even when the first absorbent portion is brought into contact with the developing liquid, and a third absorbent portion comprising a second material which is labeled with the specific enzyme and binds with the test substance, the third absorbent portion being disposed under the detecting portion, and connected to the second absorbent portion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1(a) is a schematic cross-sectional view of a conventional "liquid pot upper type" test device in a longitudinal direction thereof.

FIG. 1(b) is a schematic cross-sectional view of the "liquid pot upper type" test device before use taken on line I—I in FIG. 1(a).

FIG. 1(c) is a schematic cross-sectional view of the "liquid pot upper type" test device after use taken on line I—I in FIG. 1(a).

FIG. 2 is a schematic cross-sectional view of a conventional "spike-rupturable vacuum type" analytical test device in a longitudinal direction thereof.

FIG. 3(a) is a plan view of a first example of an analytical test device of the present invention.

FIG. 3(b) is a plan view of a second example of an analytical test device of the present invention.

FIG. 3(c) is a plan view of a third example of an analytical test device of the present invention.

FIG. 3(d) is a partial schematic perspective view of a deformable supporting member in the second example of the analytical test device of the present invention.

DESCRIPTION OF THE PREFERRED EMBODIMENTS

Other features of this invention will become apparent in the course of the following description of exemplary embodiments, which are given for illustration of the invention and are not intended to be limiting thereof.

With reference to FIGS. 3(a) to 3(c), which are schematic plan views of a first, a second and a third examples of analytical test devices of the present invention, each of the analytical test devices comprises an elongated case member 12.

Figure 4A:
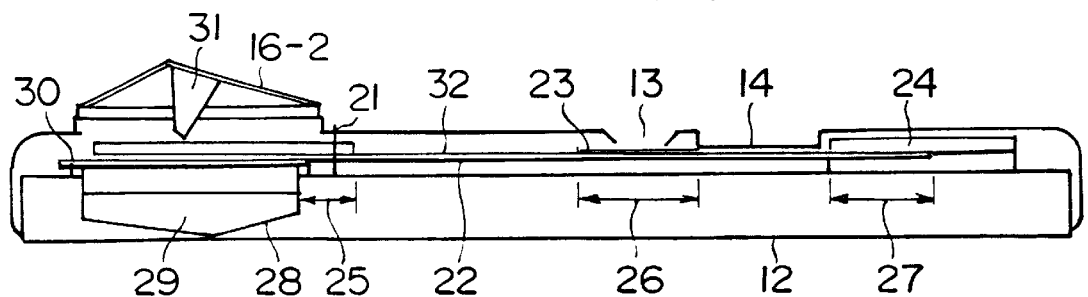
FIG. 4(a) is a schematic cross-sectional view of the second example of the analytical test device of the present invention in a longitudinal direction thereof before use.

With reference to FIG. 4(a) which is a schematic cross-sectional view of the second example of the analytical test device of the present invention in a longitudinal direction thereof before use, in an elongated case member 12, there is provided a liquid container 28 for holding a liquid 29 such as a developing liquid.

As shown in FIG. 4(a), an opening of the liquid container 28 is sealed with a sealing sheet member 30 which is impermeable, but rupturable.

Reference numeral 21 is a first absorbent portion of an analytical test strip, which is made of an absorbent material. Before this analytical test device is used, the first absorbent portion 21 is disposed on the sealing sheet member 30, out of contact with the liquid 29. However, when the first absorbent portion 21 is depressed and the sealing sheet member 30 is ruptured, and at least part of the first absorbent portion 21 is brought into contact with the liquid 29, the liquid 29 is carried through the first absorbent portion 21 by capillary action to a predetermined position, with the first absorbent portion 21 being continuously held within the liquid 29. The above-mentioned portion constitutes a liquid supply device of the present invention.

Figure 4B:
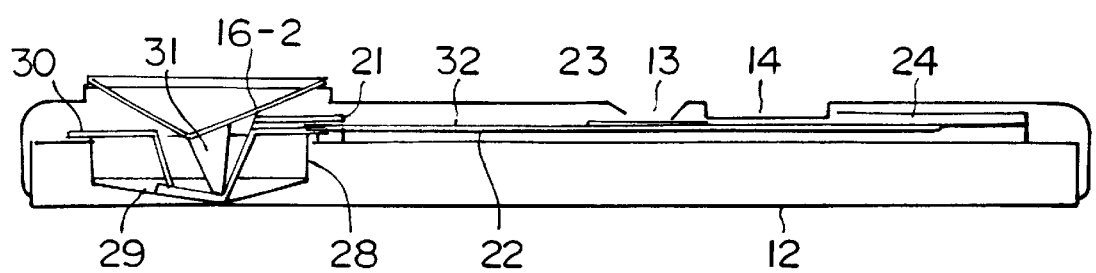
FIG. 4(b) is a schematic cross-sectional view of the second example of the analytical test device of the present invention in a longitudinal direction thereof after use.

The above-mentioned liquid supply device of the present invention may further comprise, for example, a rupturing member 31 which is capable of engaging with the first absorbent portion 21, rupturing the sealing sheet member 30 and holding part of the first absorbent portion 21 within the liquid 29 as illustrated in FIG. 4(a) and FIG. 4(b).

It is preferable that the above-mentioned rupturing member 31 be supported by a deformable supporting member 16-2 as illustrated in FIG. 4(a).

The deformable supporting member 16-2 comprises a convex portion at an inside of which the rupturing member 31 is disposed. Before use, the rupturing member 31 is positioned above the sealing sheet member 30. When depressed from the above, the deformable supporting member 16-2 is irreversibly inverted into a concave form, so that the rupturing member 31 engages with the first absorbent portion 21, then ruptures the sealing sheet member 30, brings at least part of the first absorbent portion 21 into contact with the liquid 28, and continuously holds the first absorbent portion 21 within the liquid 29 as illustrated in FIG. 4(b).

Figure 6:
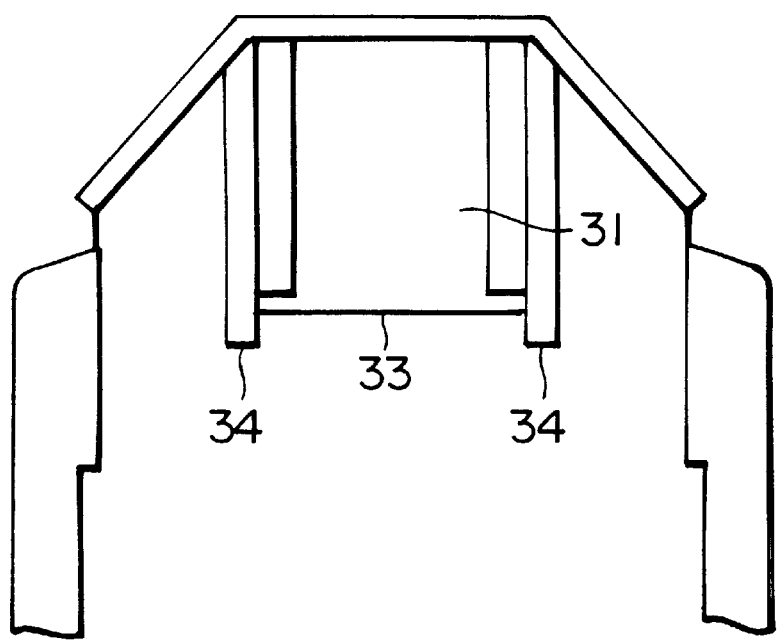
FIG. 6 is a partial schematic cross-sectional view of a deformable supporting member 16-3 in the third example of the analytical test device of the present invention, taken on line III—III in FIG. 3(c).

As illustrated in FIG. 6, it is preferable that the rupturing member 31 comprises at a top end portion thereof a pair of projected portions 34 and a concave portion 33 between the pair of the projected portions 34. In this case, in the course of the irreversible inversion of the deformable supporting member 16-2 into a concave form, the pair of projected portions 34 of the rupturing member 31 first rupture the sealing sheet member 21, and the concave portion 33 thereof engages with the first absorbent portion 21, then ruptures the sealing sheet member 30, brings at least part of the first absorbent portion 21 into contact with the liquid 29, and continuously holds the first absorbent portion 21 within the liquid 29 as illustrated in FIG. 4(b).

The deformable supporting member 16-2 is made of deformable plates and is in the form of a convex tetrahedron as illustrated in FIG. 3(b), FIG. 3(d) and FIG. 4(a) before use. The deformable supporting member 16-2, when depressed, is irreversibly inverted into a concave form as illustrated in FIG. 4(b).

A deformable supporting member 16-1 shown in FIG. 3(a) is also made of deformable plates and is in the form of a convex pentahedron as illustrated in FIG. 3(a). The deformable supporting member 16-1, when depressed, is also irreversibly inverted into a concave form in the same manner as in the deformable supporting member 16-2.

A deformable supporting member 16-3 shown in FIG. 3(c) is also made of deformable plates and is in the form of a convex tetrahedron as illustrated in FIG. 3(c), which is the same as the deformable supporting member 16-2 shown in FIG. 3(b) except that a projected stopper 20 is provided, which is for preventing the slippage of the finger when the deformable supporting member 16-3 is depressed.

In order to facilitate the inversion of, for instance, the deformable supporting member 16-2 or 16-3 as shown in FIG. 3 (b) or FIG. 3(c), and to maintain the concave form irreversibly, it is preferable that the deformable supporting member 16-2 or 16-3 comprise at least one groove-shaped portion at an outer surface or inner surface thereof at at least one position corresponding to one of ridgelines 18 and 19 in the deformable supporting member 16-2 or 16-3.

Figure 5:
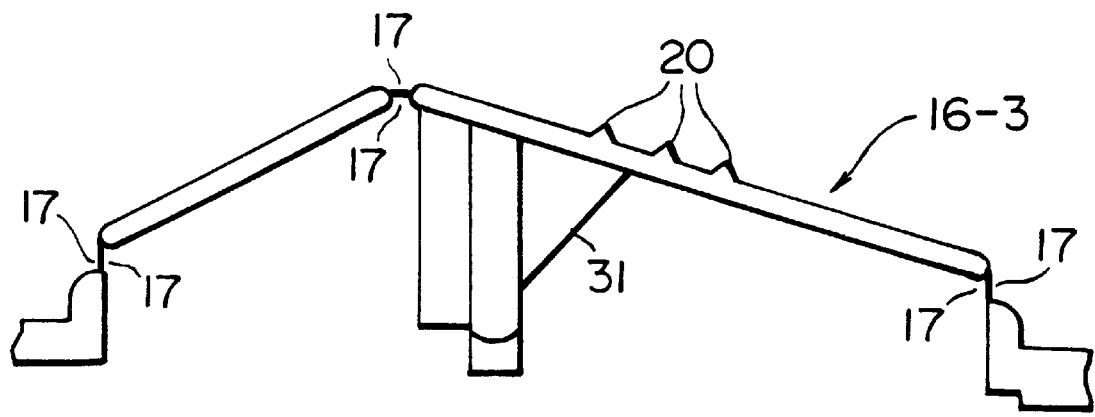
FIG. 5 is a partial schematic cross-sectional view of a deformable supporting member 16-3 in the third example of the analytical test device of the present invention, taken on line II—II in FIG. 3(c).

More specifically, with reference to FIG. 5 and FIG. 3(c), the deformable supporting member 16-3 comprises groove-shaped portions 17 at the boundaries between adjacent deformable plates of which the deformable supporting member 16-3 is composed, either at a front side or a back side of the deformable supporting member 16-3. Such groove-shaped portions may also be formed in the deformable supporting member 16-1 and the deformable supporting member 16-2. The number and positions of such groove-shaped portions in such deformable supporting members should be appropriately selected in accordance with the shape of and the material for the employed deformable supporting member.

It is preferable that the elongated case 12 and the deformable supporting member 16-1, 16-2 or 16-3 be integrally made of the same material. It is also acceptable to separately produce the elongated case 12 and the deformable supporting member 16-1, 16-2 or 16-3 in such a manner that the deformable supporting member 16-1, 16-2 or 16-3 can be incorporated into the elongated case 12 later.

It is preferable that materials for the elongated case member 12 and the deformable supporting member 16-1, 16-2 or 16-3 be plastics materials in view of the flexibility and the easiness in handling.

With reference to FIGS. 3(a) to 3(c), which are schematic plan views of the first, second and third examples of analytical test devices of the present invention, each of the analytical test devices comprises the above-mentioned liquid supply device for transporting liquid to a predetermined portion, provided that the absorbent material employed in the above is replaced by an analytical test strip comprising an absorbent material, which is capable of transporting the liquid by capillary action, the analytical test strip being disposed on the sealing sheet member, out of contact with said liquid when the sealing sheet member is not ruptured, while when the sealing sheet member is ruptured and the analytical test strip is brought into contact with the liquid, part of the test strip being continuously held within the liquid and transporting the liquid to said predetermined position, a test sample application portion 13 to which a test sample which may contain a test substance to be detected is applied so that the test sample is brought into contact with the liquid which is transported by the analytical test strip, and a detecting portion 14 for detecting a predetermined condition of the test sample in contact with one or more reagents applied to the analytical test strip at a predetermined portion upstream of the detecting portion and carried thereto by the liquid.

When an upper case member 32 is provided as illustrated in FIGS. 4(a) and 4(b), which extends from the above-mentioned deformable supporting member 16-2 so as to cover the analytical test strip comprising the first absorbent portion 21, a second absorbent portion 22 and a third absorbent portion 23, the test sample application portion 13 may be in the form of a test sample dropping window, and the detecting portion 14 may be in the form of a viewing window.

In the analytical test device according to the present invention, the analytical test strip may comprise a plurality of absorbent portions as long as each of the absorbent portions is capable of transporting the liquid by capillary action.

Specifically, the analytical test strip may comprise
a first absorbent portion comprising a substrate for a specific enzyme, part of the first absorbent portion being disposed on the sealing sheet member,
a second absorbent portion on which a first material which specifically binds with the test substance contained in the test sample is immobilized, the second absorbent portion being disposed upstream of the test sample application portion, and connected to the first absorbent portion, without being brought into contact with the liquid even when the first absorbent portion is brought into contact with the developing liquid, and
a third absorbent portion comprising a second material which is labeled with the specific enzyme and binds with said test substance, the third absorbent portion being disposed under the detecting portion, and connected to the second absorbent portion.

More specifically, with reference to FIG. 4(a), an example of the analytical test strip will now be explained.

In the first absorbent portion 21, when the specific enzyme is, for example, an alkaline phosphatase, the first absorbent portion 21 comprises, for example, an unwoven cloth with water absorption properties, which contains as the substrate a substrate which can be decomposed and colored by the above specific enzyme, for example, disodium 5-bromo-4-chloro-3-indolyl-phosphorate (BCIP) or p-nitrophenyl-phosphate.

The second absorbent portion is an absorbent portion 22, which comprises, for example, a nitrocellulose membrane on which as the first material a material such as an antigen or an antibody, which specifically binds with the test substance contained in the test sample, is mobilized.

The third absorbent portion is a third absorbent portion 23 which comprises an unwoven cloth with water absorption properties and as the second material a second material which is labeled with the specific enzyme, such as the alkaline phosphatase, and binds with the test substance, for example, an enzyme-labeled antigen or an enzyme-labeled antibody.

Thus, the analytical test strip may comprise the above-mentioned first, second and third absorbent portions 21, 22 and 23, which is elongated in the same direction as the elongated direction of the case member 12, more specifically in the direction from the liquid container 28 to the above-mentioned detecting portion 14.

The analytical test strip may be either one piece absorbent member which substantially includes the above-mentioned first, second and third absorbent portions 21, 22 and 23, or comprise the above-mentioned first, second and third absorbent portions 21, 22 and 23 which are connected to each other or overlap partly or in their entirety in such a manner that the liquid 29 can pass therethrough.

As illustrated in FIG. 4(a), one end portion of the second absorbent portion 22 and the first absorbent portion 21 partly overlap at an overlapping portion 25. The third absorbent portion 23 and the second absorbent portion 22 overlap at an overlapping portion 26 under the test sample application portion 13.

The analytical test device of the present invention may further comprise a vaporization portion 15 for vaporizing the liquid 29 as shown in rigs. 3(a) to 3(c), which is disposed downstream of the detecting portion 14 with respect to the flow of the liquid 29 through the analytical test strip, with the elongation of the analytical test strip in the direction from the liquid container 28 up to the above-mentioned vaporization portion 15. By vaporizing the liquid 29 and dispersing the same from the vaporizing portion 15, the flow of the liquid 29 through the analytical test strip can be accelerated. It is preferable that the area of the vaporization portion is larger than the total of the areas of the test sample application portion and the detecting portion.

In the above, the analytical test strip is elongated in the direction from the liquid container 28 up to the above-mentioned vaporization portion 15. In this case, the analytical test strip further comprises a fourth absorbent portion 24 which comprises, for example, an unwoven cloth with water absorption properties, free of any reagent. The fourth absorbent portion 24 and the second absorbent portion 22 overlap at an overlapping portion 27.

The analytical test strip comprises an absorbent material such as a porous material or a fibrous material through which a liquid can be transported by capillary action, for example, a filter paper comprising nitrocellulose, cellulose, or glass fiber.

The above-mentioned liquid container 28 for holding the liquid therein for use in the analytical test device of the present invention includes an opening. The opening is sealed with the sealing sheet member 30, which is, for example, made of an aluminum film. As mentioned above, the liquid container 28 is incorporated into the case member 12. The term "incorporated" here means not only that the liquid container 28 is included in the case member 12 in the sense that the liquid container 28 and the case member 12 are physically separable members, but also means that the liquid container 28 is part of the case member 12 in the sense that the liquid container 28 and the case member 12 constitute an integral member that cannot be separated.

In the analytical test device of the present invention, one or more reagents can be applied to the absorbent material at the test sample application portion. Alternatively, the one or more reagents may be contained in the liquid held the liquid container 28.

When the analytical test device of the present invention is used in practice, a predetermined amount of a test sample which may contain a test substance to be detected is applied to the detecting portion 13, and the deformable supporting member 16-1, 16-2 or 16-3 is depressed in such a manner that at least part of the first absorbent portion 21 of the analytical test strip is caused to stay in the liquid 29 held in the container 28. In a predetermined period of time, the condition of the test sample, for example, a color thereof, is visually inspected at the detecting portion 14, whereby the presence or absence of the test substance to be detected can be determined, or a positive or negative evaluation of the test sample can be performed. When a calorimetric detection can be performed, colorimetry can also be performed, using a calorimeter.

When the liquid supply device of the present invention is used, a predetermined amount of a liquid can be securely supplied to an absorbent material or an analytical test strip at a predetermined constant rate, so that the liquid supply device can be used not only for an analytical test device for immunoassay, but also for a device for spreading from the absorbent material a perfume or an insecticide in a room.

Furthermore, in the analytical test device of the present invention, part of the analytical test strip is pushed into the liquid container so as to bring the part of the analytical test strip into contact with the liquid such as a developing liquid held in the liquid container, and to transport the liquid only by capillary action for the analysis. Therefore, there is no risk that the liquid is rushed onto the analytical test strip. Furthermore, once the analytical test device is used, the deformable supporting member is irreversibly deformed, so that whether the analytical test device has been used or has not yet been used can be seen at first glance.

What is claimed is:

1. A liquid supply device for transporting a liquid to a predetermined portion, comprising:
   a liquid container for holding a liquid therein, which comprises an opening,
   a sealing sheet member which is impermeable but rupturable and seals said opening of said container, and
   an absorbent material which is capable of transporting said liquid by capillary action, said absorbent material being disposed on said sealing sheet member, out of contact with said liquid when said sealing sheet member is not ruptured, while when said sealing sheet member is ruptured and said absorbent material is brought into contact with said liquid, part of said absorbent material being continuously held within said liquid and transporting said liquid to said predetermined position.

2. The liquid supply device as claimed in claim 1, further comprising a rupturing member which is capable of engaging with said absorbent material, rupturing said sealing sheet member and holding part of said absorbent material within said liquid.

3. The liquid supply device as claimed in claim 2, further comprising a deformable supporting member for supporting said rupturing member, said deformable supporting member comprising a convex portion which can be irreversibly inverted into a concave form when depressed, thereby holding said rupturing member in such a position that said sealing sheet member is ruptured and part of said absorbent material is continuously held within said liquid.

4. The liquid supply device as claimed in claim 3, wherein said deformable supporting member comprises at least one groove-shaped portion for facilitating the irreversible inverting of said convex portion into said concave form and maintaining said concave form when depressed.

5. An analytical test device comprising:
   a liquid supply device for transporting liquid to a predetermined portion, comprising:
   a) a liquid container for holding a liquid therein, which comprises an opening,
   b) a sealing sheet member which is impermeable but rupturable and seals said opening of said liquid container, and
   c) an analytical test strip comprising an absorbent material, which is capable of transporting said liquid by capillary action, said analytical test strip being disposed on said sealing sheet member, out of contact with said liquid when said sealing sheet member is not ruptured, while when said sealing sheet member is ruptured and said analytical test strip is brought into contact with said liquid, part of said test strip being continuously held within said liquid and transporting said liquid to said predetermined position,
   a test sample application portion to which a test sample which may contain a test substance to be detected is applied so that said test sample is brought into contact with said liquid which is transported by said analytical test strip, and
   a detecting portion for detecting a predetermined condition of said test sample in contact with one or more reagents applied to said analytical test strip at a predetermined portion upstream of said detecting portion and carried thereto by said liquid.

6. The analytical test device as claimed in claim 5, wherein said liquid supply device further comprises a rupturing member which is capable of engaging with said analytical test strip, rupturing said sealing sheet member and holding part of said analytical test strip within said liquid.

7. The analytical test device as claimed in claim 5, wherein said liquid supply device further comprises a deformable supporting member for supporting said rupturing member, said deformable supporting member comprising a convex portion which can be irreversibly inverted into a concave form when depressed, thereby holding said rupturing member in such a position that said sealing sheet member is ruptured and part of said analytical test strip is continuously held within said liquid.

8. The analytical test device as claimed in claim 7, wherein said deformable supporting member in said liquid supply device comprises at least one groove-shaped portion for facilitating the irreversible inverting of said convex portion into said concave form and maintaining said concave form when depressed.

9. The analytical test device as claimed in claim 5, wherein said one or more reagents are applied to said absorbent material at said test sample application portion.

10. The analytical test device as claimed in claim 5, wherein said one or more reagents are contained in said liquid in said liquid container.

11. The analytical test device as claimed in claim 5, further comprising a vaporization portion, which is disposed downstream of said detecting portion with respect to the flow of said liquid through said analytical test strip, wherein the area of said vaporization portion is larger than the total of the areas of said test sample application portion and said detecting portion.

12. The analytical test device as claimed in claim 5, wherein said analytical test strip comprises a plurality of absorbent portions, each of which is capable of transporting said liquid by capillary action.

13. The analytical test device as claimed in claim 12, wherein said analytical test strip comprises:
   a first absorbent portion comprising a substrate for a specific enzyme, part of said first absorbent portion being disposed on said sealing sheet member,
   a second absorbent portion on which a first material which specifically binds with said test substance contained in said test sample is immobilized, said second absorbent portion being disposed upstream of said test sample application portion, and connected to said first absorbent portion, without being brought into contact with said liquid even when said first absorbent portion is brought into contact with said developing liquid, and
   a third absorbent portion comprising a second material which is labeled with said specific enzyme and binds with said test substance, said third absorbent portion being disposed under said detecting portion, and connected to said second absorbent portion.

* * * * *